(12) United States Patent
Everett et al.

(10) Patent No.: US 6,466,713 B2
(45) Date of Patent: Oct. 15, 2002

(54) OPTICAL FIBER HEAD FOR PROVIDING LATERAL VIEWING

(75) Inventors: Matthew J. Everett; Billy W. Colston, both of Livermore; Dale L. James, Tracy; Steve Brown, Livermore; Luiz Da Silva, Danville, all of CA (US)

(73) Assignee: The Regents of the University of California, Oakland, CA (US)

( * ) Notice: Subject to any disclaimer, the term of this patent is extended or adjusted under 35 U.S.C. 154(b) by 1 days.

(21) Appl. No.: 09/883,513

(22) Filed: Jun. 18, 2001

(65) Prior Publication Data

US 2002/0021866 A1 Feb. 21, 2002

Related U.S. Application Data

(60) Provisional application No. 60/226,165, filed on Aug. 18, 2000.

(51) Int. Cl.⁷ .................................................. G02B 6/26
(52) U.S. Cl. ......................... 385/31; 385/116; 385/119
(58) Field of Search ............................ 385/31, 32, 116, 385/117, 119; 606/15

(56) References Cited

U.S. PATENT DOCUMENTS

| | | | |
|---|---|---|---|
| 5,321,501 A | 6/1994 | Swanson et al. | 356/345 |
| 5,459,570 A | 10/1995 | Swanson et al. | 356/345 |
| 6,110,105 A | * 8/2000 | Durell | 600/173 |
| 6,134,003 A | 10/2000 | Tearney | 356/345 |
| 6,175,669 B1 | 1/2001 | Colston | 385/12 |

FOREIGN PATENT DOCUMENTS

| | | |
|---|---|---|
| WO | WO 9219930 | 9/1992 |
| WO | WO 97/32182 | 9/1997 |
| WO | WO 9838907 | 9/1998 |
| WO | WO 0042906 | 7/2000 |

OTHER PUBLICATIONS

Xingde Li et al "Imaging needle for optical coherence tomography" Optics Letters vol. 25, No. 20/ Oct. 15, 2000 p. 1520–1522.

* cited by examiner

*Primary Examiner*—Robert H. Kim
*Assistant Examiner*—Elizabeth Gemmell
(74) *Attorney, Agent, or Firm*—James M. Skorich; Alan H. Thompson

(57) ABSTRACT

The head of an optical fiber comprising the sensing probe of an optical heterodyne sensing device includes a planar surface that intersects the perpendicular to axial centerline of the fiber at a polishing angle θ. The planar surface is coated with a reflective material so that light traveling axially through the fiber is reflected transverse to the fiber's axial centerline, and is emitted laterally through the side of the fiber. Alternatively, the planar surface can be left uncoated. The polishing angle θ must be no greater than 39° or must be at least 51°. The emitted light is reflected from adjacent biological tissue, collected by the head, and then processed to provide real-time images of the tissue. The method for forming the planar surface includes shearing the end of the optical fiber and applying the reflective material before removing the buffer that circumscribes the cladding and the core.

30 Claims, 3 Drawing Sheets

OPTICAL FIBER HEAD FOR PROVIDING LATERAL VIEWING

This application claims benefit of Provisional application No. 60/226,165 filed Aug. 18, 2000.

The United States Government has rights in this invention pursuant to Contract No. W-7405-ENG-48 between the United States Department of Energy and the University of California for the operation of Lawrence Livermore National Laboratory.

BACKGROUND OF THE INVENTION

The invention relates generally to optical fibers and, more particularly, to optical fibers providing lateral viewing for use during medical procedures.

Optical coherence domain reflectometry ("OCDR") is described in R. C. Youngquist et al, "Optical Coherence-Domain Reflectometry: A New Optical Evaluation Technique," *Optics Letters*, Vol. 12, No.3, pp. 158–160, (1987). B. L Danielson et al, "Guided-Wave Reflectometry with Micrometer Resolution," *Applied Physics*, Vol.26, No. 14, pp. 2836–2842, (1987), describes an optical reflectometer that uses a scanning Michelson interferometer in conjunction with a broadband illuminating source and cross-correlation detection. The first application of OCDR to diagnose biological tissue is noted in X. Clivaz et al, "High-Resolution Reflectometry in Biological Tissues," *Optics Letters*, Vol. 1, No.1, pp. 4–6, (1992). The similar technique of optical coherence tomography ("OCT") has been used for imaging with catheters, as disclosed in U.S. Pat. Nos. 5,321,501 and 5,459,570 issued to E. A. Swanson et al.

Both OCDR and OCT use optical data collected by a single mode optical fiber to determine the morphology, physical properties and location of various types of interspersed biological tissue. More particularly, a probe used in conjunction with either OCDR and OCT is typically comprised of an optical fiber having a head at its distal tip. Alternatively, the probe is formed by inserting an optical fiber concentrically into a thin-wall flexible hypodermic stainless-steel tube and fastening it therein with cement. A window in the tube allows light to pass to and from the head at the tip of the optical fiber. The probe is then inserted into the tissue or organ to be examined. Light emitted by the head of the optical fiber is reflected from the adjacent body of tissue or organ. The head then collects the reflected light, also known as "back-scattered" light.

Using a Michelson interferometer in conjunction with techniques and apparatus discussed in the aforementioned references, the elapsed time necessary for each light ray to return to the fiber is calculated. From this data, the morphology, properties and location of the various tissue or organ elements that caused the back-scattered light are determined and an image generated to provide a real-time visual display of the body of tissue or organ being examined.

The real-time image provided by OCDR and OCT has been used to great advantage in conjunction with medical procedures. However, as a typical optical fiber can only emit light and gather back-scattered light along its axial centerline, it is limited to viewing straight ahead. A view transverse to the axial centerline of the fiber can only be obtained by turning or bending the head of the fiber perpendicular to its axial centerline, and this is often very difficult or even impossible in the close confines typically encountered during surgical procedures, e.g., in examining the sides of an artery or vein.

One solution to this problem is to mount a gradient refractive index ("GRIN") lens or a mirrored corner cube on the head of the optical fiber. Both of these devices deflect the emitted light at an angle transverse to the axial centerline of the optical fiber, and thus provide for lateral viewing. However, these apparatus add bulk to the head of the optical fiber. For example, the diameter of an optical fiber typically used in conjunction with OCDR and OCT is 90 microns ($10^{-6}$ meter), while the diameter of the smallest GRIN lens is 150 microns and that of the smallest mirrored corner cube is 125 microns. The use of either of the aforementioned optical devices thus renders some locations inaccessible and makes the optical fiber more difficult to maneuver. In addition, extremely small GRIN lenses and mirrored corner cubes are quite expensive, and very fragile. Their use thus adds to the cost of the probe, and renders it prone to malfunction.

As may be seen from the foregoing, there presently exists a need in the art for an optical fiber head that provides for lateral viewing without increasing the size of the fiber head. The present invention fulfills this need in the art, and does so without adversely affecting the reliability of the optical sensing probe and at significantly less cost than the prior art devices used for this purpose.

SUMMARY OF THE INVENTION

Briefly, the present invention is a modification to the head of a single mode optical fiber comprising the sensing probe of an optical heterodyne sensing system, such as an OCDR or OCT device, which enables optical sensing transverse to the axial centerline of the fiber. The optical fiber including the present invention is typically incorporated into a catheter, endoscope, or other medical device to determine the location, thickness, and morphology of the arterial walls or other intra-cavity regions during a minimally invasive medical procedure. The information is used to guide the sensing probe through the body as well as evaluate the tissue through which the sensing probe is being passed.

More particularly, a planar surface is formed at the end of an optical fiber, with the surface intersecting the perpendicular to the axial centerline of the optical fiber at an acute polishing angle. The surface is coated with a reflective material so that light traveling axially through the fiber is reflected at an emission angle relative to the axial centerline of the fiber, and passes through the side of the fiber. Alternatively, the planar surface can be left uncoated. In the latter case, total internal reflection occurs due to the differential in density between the core of the optical fiber and the adjacent tissue or fluid. To avoid internal reflection from the side of the optical fiber that occurs when the emission angle is too close to 90°, the polishing angle should be at least 51° or, alternatively, no greater than 39°.

A portion of the emitted light is reflected by biological tissue and collected by the fiber head. Processing the back-scattered light using OCDR or OCT techniques and apparatus provides images of tissue located lateral to the optical fiber. The maximum or minimum polishing angle is determined primarily by the extent to which it is desired to deviate from a view normal to the side of the optical fiber, rather than by limitations arising from optical mechanics.

The present invention provides for viewing biological tissue transverse to the axial centerline of an optical fiber comprising a sensing probe, without increasing the size of the fiber head. It also achieves the foregoing without compromising the durability of the sensing probe or adding substantial cost to its manufacture.

The present invention also includes the method for modifying the optical fiber to obtain the aforementioned configuration. The end of the optical fiber is first cut at the proper polishing angle. The resulting planar surface is then polished with the circumferential buffer intact, rather that stripping the buffer before polishing as is usually done. The fiber is then coated with a reflecfive material using a standard technique such as sputter coating. Alternatively, the foregoing step may be omitted.

Next, the buffer is stripped from the end of the fiber. Stripping the buffer at this point also removes any reflective material that may have overlapped onto the buffer. Finally, the head is coated with a transparent protective material.

DETAILED DESCRIPTION OF THE INVENTION

Figure 1:
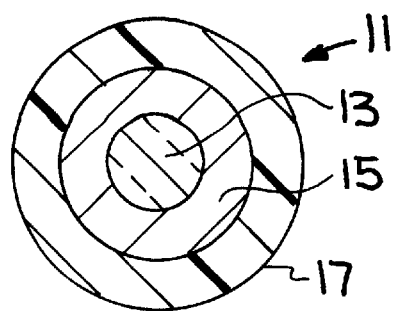
FIG. 1 is a front view of a single mode optical fiber.
Figure 2:
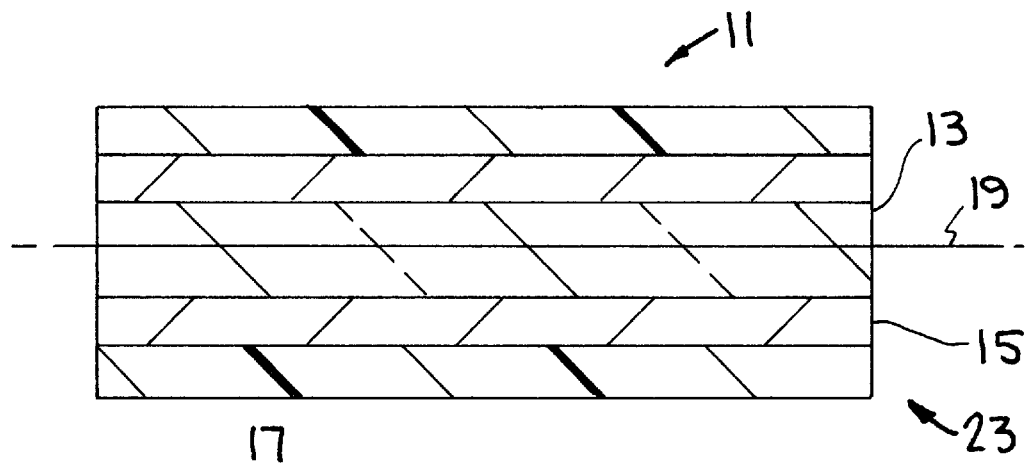
FIG. 2 is a side section view of a single mode optical fiber.

Turning to the drawings, FIG. 1 shows a front section view of single mode optical fiber 11. FIG. 2 is a side section view of fiber 11. Fiber 11 is comprised of cylindrical core 13, circumferential cladding 15, and circumferential buffer 17. Fiber 11 includes axial centerline 19, perpendicular 20 to axial centerline 19, and distal end 23. The method of the present invention is used to form reflective head 27, illustrated in FIG. 4, from distal end 23 of fiber 11.

Figure 3:
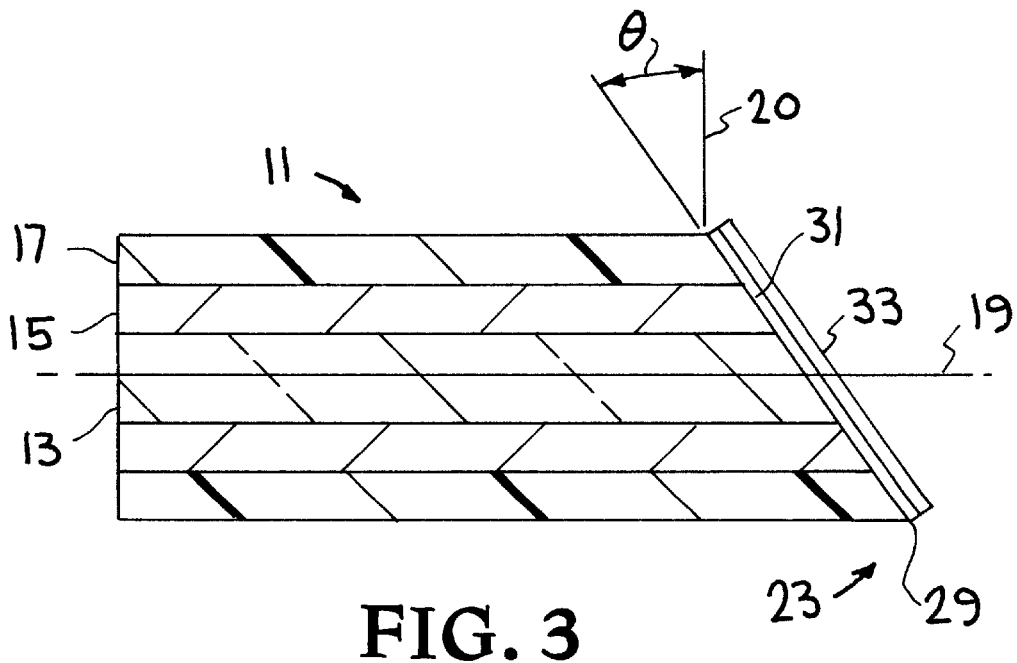
FIG. 3 is a side section view of a single mode optical fiber having a planar surface at one end formed by a transverse cut.

As shown in the side section view of FIG. 3, a transverse cut is made across distal end 23 to form planar surface 29 at a polishing angle θ with respect to perpendicular 20. As will be subsequently discussed in greater detail, θ should either be at least 51° or no greater than 39°; that is, θ should lie outside of an exclusion angle range bounded by a value greater than 39° to any value less than 51°. Planar surface 29 is then polished and coated with reflective material 31, e.g., aluminum, using any one of several techniques known to those skilled in the relevant art, e.g., sputter coating.

Light must pass through the side of fiber 11 near distal end 23 after being reflected from reflective material 31. To avoid obstructing the reflected light, reflective material 31 must not cover the side of fiber 11. Thus, planar surface 29 is polished and coated with reflective material 31 with buffer 17 intact, rather than stripping away buffer 17 before polishing and coating surface 29.

Figure 4:
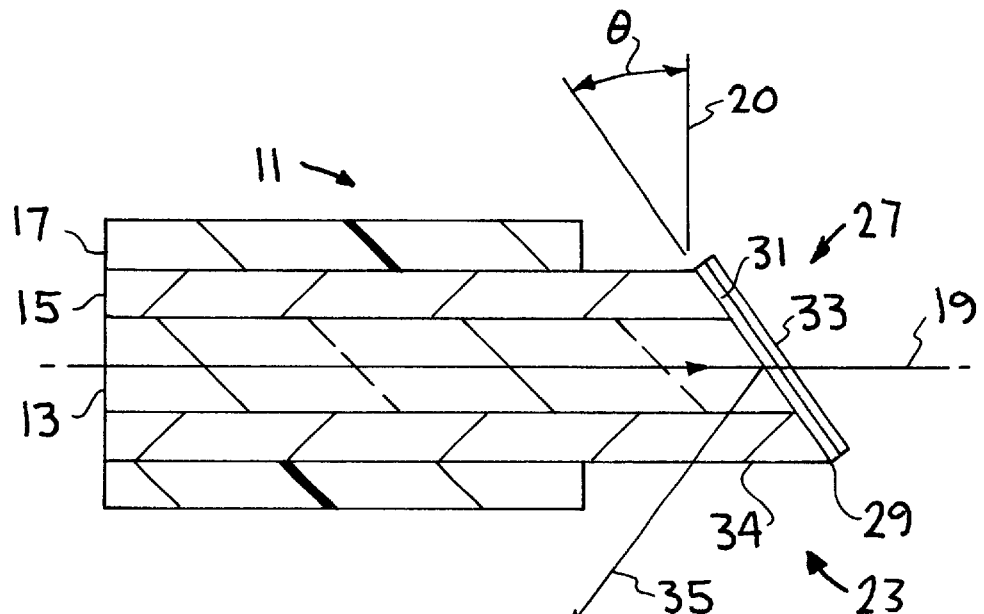
FIG. 4 is a side section view of a single mode optical fiber having the head of the present invention at one end.

FIG. 4 shows distal end 23 with buffer 17 removed, to form reflective head 27. Any reflective material 31 that overlapped planar surface 29 and became attached to buffer 17 is thus removed along with buffer 17, leaving core 13 and cladding 15 unobstructed. Alternatively, the application of reflective material 31 may be omitted.

The formation of head 27 is completed by coating reflective material 31 with transparent material 33 to protect reflective material 31 and to smooth any rough edges around the circumference of planar surface 29 and reflective material 31. If reflective material 31 is not applied, transparent material 33 is applied directly to planar surface 29.

Figure 5:
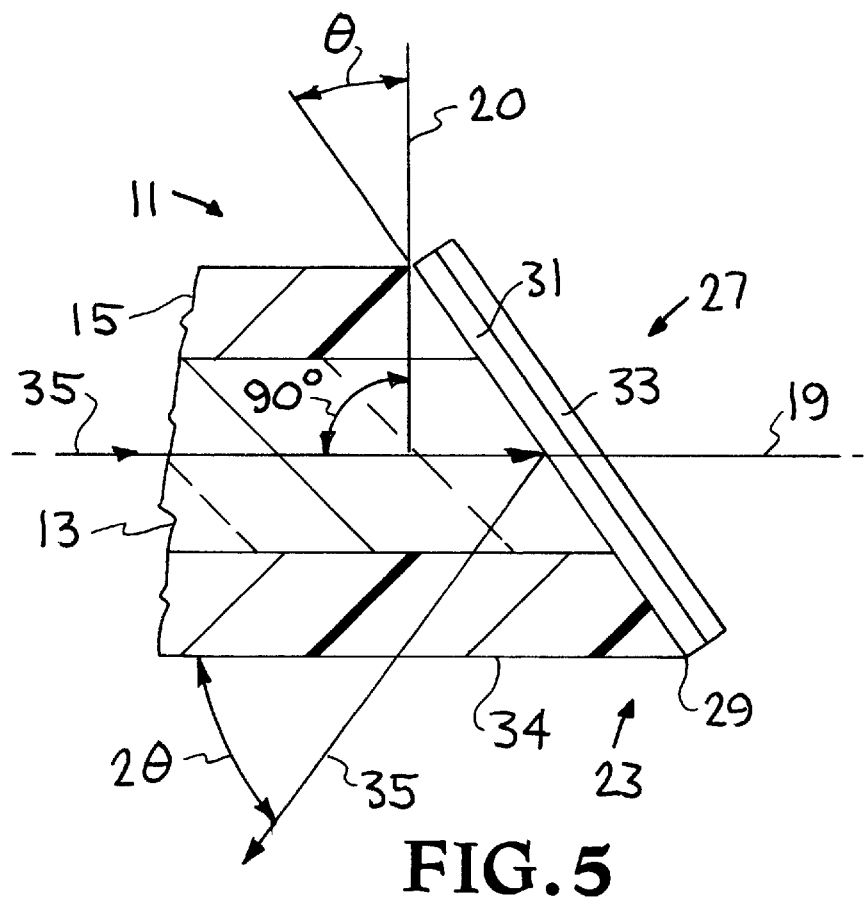
FIG. 5 is a schematic diagram showing the geometric relationship of the polishing angle, θ, and the emission angle, 2θ, with the axial centerline and sides of the optic fiber.

FIG. 5 shows the geometric relationship between polishing angle θ, centerline 19, perpendicular 20, side 34 of cladding 15, and emission angle 2θ. Light ray 35 impinges reflective material 31 at planar surface 29 and is reflected therefrom, through cladding 15, and out of side 34 at emission angle 2θ with respect to side 34. When polishing angle θ is less than 45°, emission angle 2θ is acute and ray 35 is reflected generally backward relative to its original direction within core 13. When polishing angle θ equals 45°, emission angle 2θ is 90° and thus normal to side 34. When polishing angle θ is greater than 45°, emission angle 2θ is obtuse and ray 35 is reflected generally in its original forward direction within core 13.

When θ equal 45° (and 2θ equals 90°), so much of ray 35 is reflected off of side 34 and back into fiber 11 that the emitted portion does not provide meaningful backscattering. To avoid the problem of internal reflection, it has been found that θ must be no greater than 39°, or at least 51°. Stated alternatively, θ should lie outside of an exclusion angle range bounded by a value greater than 39° to less than 51°. The resultant differential between the emission angle 2θ and perpendicular 20 reduces the internal reflection enough to emit a light ray 35 of sufficient intensity to generate meaningful back-scattering. The maximum or minimum polishing angle θ is determined primarily by the extent to which it is acceptable to deviate from a view nearly normal to side 34, rather than by limitations arising from optical mechanics.

Figure 6:
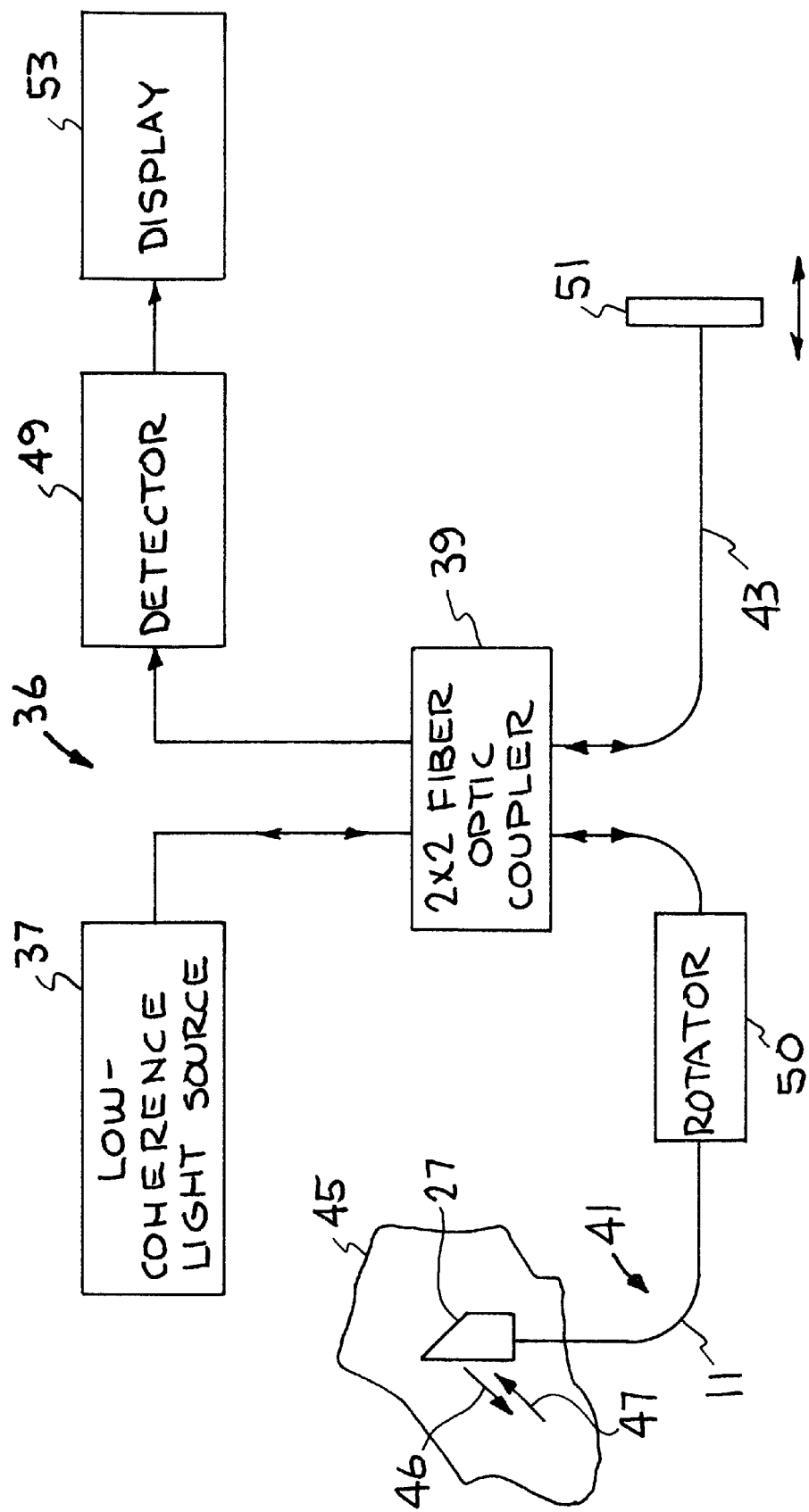
FIG. 6 is schematic diagram of a conventional OCDR scanning system incorporating the optical fiber head of the present invention.

FIG. 6 is a schematic drawing of OCDR scanning apparatus 36 incorporating reflective head 27 of the present invention. Light from low-coherence light source 37 is input into a 2×2 fiber optic coupler 39, which splits the light and directs it into sensing probe 41 and reference arm 43. Sensing probe 41 includes optical fiber 11 and head 27. Head 27 comprises the distal end of sensing probe 41, and is inserted into a patient to scan tissue 45.

Light rays 46 in sensing probe 41 travel along core 13 of optical fiber 11 until impinging reflective material 31. Light rays 46 are then reflected and emitted from head 27 transverse to axial centerline 19, and into adjacent tissue 45. After being reflected from various interspersed elements in tissue 45, back-scattered light rays 47 are collected by head 27 for travel back through sensing probe 41 and 2×2 fiber optic coupler 39, en route to detector 49. Head 27 thus provides back-scattered light from elements of tissue 45 lying lateral to head 27, i.e., transverse to centerline 19.

Rotator 50 rotates sensing probe 41, and thus head 27, about axial centerline 19. The rotation of head 27 about axial centerline 19 provides back-scattered light from elements of tissue 45 circumscribing head 27.

In another embodiment, planar surface 29 is not coated with reflective material 31. Reflection of light incident upon planar surface 29 occurs due to the difference in density, and thus in the index of refraction, between core 13 and adjacent body fluids or tissue 45.

Reference arm 43 includes mirror 51. Light input into reference arm 43 is reflected by mirror 51 back to 2×2 fiber optic coupler 39. Mirror 51 can be translated to vary the path length of reference light traveling between mirror 51 and 2×2 fiber optic coupler 39. This provides a variable delay for the reference light traveling through reference arm 43.

The reference light reflected from mirror 51 in reference arm 43 and back-scattered light rays 47 from sensing probe 41 pass back through 2×2 fiber optic coupler 39 to detector 49. Detector 49 uses processing electronics and techniques well known in the art to produce a back-scatter profile, or "image," of tissue 45 on display 53. In essence, detector 49 determines the density and distance of the various interspersed elements of tissue 45 by measuring, firstly, the intensity of back-scattered light rays 47 and, secondly, the time necessary for light rays 47 to travel between the tissue element causing a reflection and detector 49. The travel time is calculated by a Michelson interferometer that uses the reference light reflected from mirror 51 to measure the phase shift in back-scattered light rays 47.

It is to be understood, of course, that the foregoing description relates to several embodiments of the invention and that modifications may be made without departing from the spirit and scope of the invention as set forth in the following claims.

We claim:

1. An apparatus for examining matter using light comprising:

an optical fiber having an axial centerline;

the optical fiber including a planar surface intersecting the axial centerline for reflecting light transverse to the axial centerline;

a plane perpendicularly intersecting the axial centerline;

a polishing angle formed by an intersection of the plane and the planar surface; and the polishing angle lying outside of an exclusion angle range of, at least, greater than 39° to less than 51°, whereby light travels within the optical fiber until being reflected at the planar surface and emitted from the optical fiber transverse to the axial centerline.

2. The optical apparatus as defined in claim 1 wherein the exclusion angle range is 39° to 51°.

3. The optical apparatus as defined in claim 1 wherein the exclusion angle range is greater than 38° to less than 52°.

4. The optical apparatus as defined in claim 1 wherein the exclusion angle range is 38° to 52°.

5. The optical apparatus as defined in claim 1 wherein the exclusion angle range is greater than 37° to less than 53°.

6. The optical apparatus as defined in claim 1 wherein the optical fiber has a distal end that includes the planar surface.

7. The optical apparatus as defined in claim 6 wherein the planar surface is coated with a reflective material.

8. The optical apparatus as defined in claim 7 wherein:

the planar surface is for reflecting light that has been back-scattered from the matter being examined, into the optical fiber; and the optical fiber is also for transmitting the back-scattered light to a detector means for generating an image of the matter being examined.

9. The optical apparatus as defined in claim 1 wherein:

the optical fiber is cylindrical, and is comprised of concentric layers including an opaque buffer, a cladding, and a core; and the planar surface intersects only the cladding and the core.

10. The optical fiber as defined in claim 9 further comprising:

an unsymmetrical separation gap intermediate the buffer and the planar surface;

the separation gap having a maximum value and a minimum value; and light being emitted from the optical fiber by passing through the separation gap at the maximum value.

11. The optical apparatus as defined in claim 1 wherein:

the optical fiber is cylindrical and comprised of concentric layers including an opaque buffer, a cladding, and a core;

the buffer lies outside of the cladding, and the cladding lies outside of the core; and the buffer extends to an axial station short of the planar surface, so that the planar surface intersects only the cladding and the core.

12. The optical apparatus as defined in claim 1 wherein:

the optical fiber is comprised of concentric layers including an opaque buffer, a cladding, and a core;

the buffer lies outside of and abuts the cladding, with the abutment forming a cylinder;

the cladding lies outside of the core; and the cylinder fails to intersect the planar surface.

13. The optical fiber as defined in claim 9 wherein the planar surface is coated with a transparent material.

14. The optical apparatus as defined in claim 9 wherein the planar surface is coated with a reflective material.

15. The optical apparatus as defined in claim 14 wherein the reflective material is coated with a transparent material.

16. The optical apparatus as defined in claim 14 wherein the reflective coating is comprised of aluminum.

17. A method for forming a reflective head at an end of an optical fiber having a buffer circumscribing a core, comprising the steps of:

forming a planar surface at the end; and subsequently removing the buffer.

18. The forming method as recited in claim 17 comprising coating the planar surface with a reflective material before removing the buffer.

19. The forming method as recited in claim 18 wherein:

the optical fiber is provided with an axial centerline and a plane that perpendicularly intersects the axial centerline; comprising forming a polishing angle by an intersection of the plane and the planar surface; and forming the planar surface with the polishing angle lying outside an exclusion angle range of, at least, over 39° to under 51°.

20. The forming method as recited in claim 19 wherein the exclusion angle range is 39° to 51°.

21. The forming method as recited in claim 19 wherein the exclusion angle range is over 38° to under 52°.

22. The forming method as recited in claim 19 wherein the exclusion angle range is 38° to 52°.

23. The forming method as recited in claim 19 wherein the exclusion angle range is over 37° to under 53°.

24. The forming method as recited in claim 19 comprising coating the reflective material with a transparent material.

25. An apparatus for examining matter with light comprising:

an optical fiber having an axial centerline;

the optical fiber including a planar surface oriented at a polishing angle with respect to a plane perpendicularly intersecting the axial centerline, for reflecting light to a course transverse to the axial centerline, and for collecting back-scattered light reflected from the matter being examined;

the polishing angle lying outside an exclusion angle range of, at least, over 39° to under 51°; and means for interfering the back-scattered light with reference light, whereby an image of the matter being examined is generated.

26. The optical apparatus as defined in claim 25 wherein the exclusion angle range is 39° to 51°.

27. The optical apparatus as defined in claim 25 wherein the exclusion angle range is over 38° to under 52°.

28. The optical apparatus as defined in claim 25 wherein the exclusion angle range is 38° to 52°.

29. The optical apparatus as defined in claim 25 wherein the exclusion angle range is over 37° to under 53°.

30. The optical apparatus as defined in claim 25 further comprising means for rotating the optical fiber around the axial centerline.

* * * * *